United States Patent
Fukushima

(10) Patent No.: US 7,732,517 B2
(45) Date of Patent: Jun. 8, 2010

(54) ORGANOSILICON COMPOUNDS AND RUBBER COMPOSITIONS MADE BY USING THE SAME

(75) Inventor: Yasuo Fukushima, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 25 days.

(21) Appl. No.: 12/094,562

(22) PCT Filed: Nov. 21, 2006

(86) PCT No.: PCT/JP2006/323181

§ 371 (c)(1),
(2), (4) Date: May 21, 2008

(87) PCT Pub. No.: WO2007/060934

PCT Pub. Date: May 31, 2007

(65) Prior Publication Data

US 2009/0247683 A1    Oct. 1, 2009

(30) Foreign Application Priority Data

Nov. 25, 2005    (JP)    ............... 2005-340691

(51) Int. Cl.
| B60C 1/00 | (2006.01) |
| B60C 5/00 | (2006.01) |
| C08K 5/24 | (2006.01) |
| C08K 3/10 | (2006.01) |
| C08K 3/04 | (2006.01) |
| C04B 26/06 | (2006.01) |
| C07F 7/04 | (2006.01) |
| C07F 7/08 | (2006.01) |
| C08F 36/00 | (2006.01) |
| C08F 136/00 | (2006.01) |

(52) U.S. Cl. .................. 524/262; 556/427; 524/437; 524/492; 526/335; 152/450

(58) Field of Classification Search .............. 528/33, 528/35, 30, 32, 38; 556/427; 524/262
See application file for complete search history.

(56) References Cited

U.S. PATENT DOCUMENTS

| 3,842,111 A | * 10/1974 | Meyer-Simon et al. ...... 556/428 |
| 5,563,231 A | 10/1996 | Barringer, Jr. et al. |
| 6,022,923 A | * 2/2000 | Araki et al. ................. 524/494 |
| 6,433,206 B1 | 8/2002 | Gedon et al. |
| 6,624,230 B2 | * 9/2003 | Luginsland .................. 524/492 |
| 6,673,954 B1 | 1/2004 | Gedon et al. |
| 7,323,582 B2 | * 1/2008 | Deschler et al. ............. 556/427 |
| 2003/0130388 A1 | 7/2003 | Luginsland et al. |
| 2005/0004386 A1 | * 1/2005 | Deschler et al. ............. 556/457 |
| 2006/0025506 A1 | 2/2006 | Weller et al. |

FOREIGN PATENT DOCUMENTS

| EP | 0 949 263 A2 | 10/1999 |
| EP | 1 285 926 A1 | 2/2003 |
| GB | 1 500 363 A | 2/1978 |
| JP | 50-108225 A | 8/1975 |
| JP | 10-36513 A | 2/1998 |
| JP | 2000-103794 A | 4/2000 |
| JP | 2002-275311 A | 9/2002 |
| JP | 2003-201295 A | 7/2003 |
| JP | 2005-35889 A | 2/2005 |
| JP | 2005-510520 A | 4/2005 |
| WO | 03/016387 A1 | 2/2003 |
| WO | 2006/015010 A2 | 2/2006 |

* cited by examiner

*Primary Examiner*—Vasu Jagannathan
*Assistant Examiner*—Anthony H Sheh
(74) *Attorney, Agent, or Firm*—Sughrue Mion, PLLC

(57) ABSTRACT

An organosilicon compound having a structure represented by following general formula:

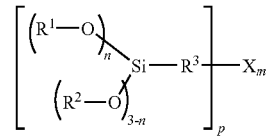

$R^1$: methyl group or ethyl group, $R^2$: a branched or linear, saturated or unsaturated aliphatic hydrocarbon group having 3 to 8 carbon atoms, n: 0.5~2.5 (an average composition), $R^3$: a divalent hydrocarbon group of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH(CH_3)$—, —$CH_2CH(CH_3)$—, —$C(CH_3)_2$—, —$CH(C_2H_5)$—, —$CH_2CH_2CH(CH_3)$— or —$CH_2CH(CH_3)CH_2$—, X: S, S(C=O)—$R^4$, SH or $NH_{(3-p)}$, and $R^4$: a branched or linear, saturated or unsaturated aliphatic hydrocarbon group having 1 to 30 carbon atoms. When X=S, p=2 and m=1~10. When X=S(C=O)—$R^4$, p=1 and m=1. When X=SH, p=1 and m=1. When X=$NH_{(3-p)}$, p=1~3 and m=1. The organosilicon compound simultaneously suppresses discharge of volatile alcohols generated during the reaction with an inorganic filler and exhibits great reactivity with the inorganic filler.

5 Claims, No Drawings

ORGANOSILICON COMPOUNDS AND RUBBER COMPOSITIONS MADE BY USING THE SAME

TECHNICAL FIELD

The present invention relates to an organosilicon compound which enhances the reinforcing property of an inorganic filler mixed with rubber, a rubber composition comprising the compound and a pneumatic tire prepared by using the rubber composition.

BACKGROUND ART

Various rubber compositions for tire treads in which an inorganic filler such as silica is added to a diene-based rubber such as natural rubber and/or synthetic rubber used as the rubber component have been proposed so that suppressed fuel consumption and excellent gripping property on wet roads are simultaneously exhibited.

When the bonding strength in a rubber composition using an inorganic filler such as silica is compared with that of conventional rubber compositions using carbon black, the bonding between the inorganic filler and the rubber component is smaller than the bonding between carbon black and the rubber component.

In the rubber composition using silica or the like, in general, a silane coupling agent which is an organosilicon compound is used for enhancing the bonding between the inorganic filler and the rubber component. The silane coupling agent enhances the bonding between the inorganic filler and the rubber component and improves abrasion resistance of a tire tread. In particular, silane coupling agents which are organosilicon compounds having a combination of an alkoxysilyl group and sulfur in the molecule are preferable since the inorganic filler such as silica and the rubber component are easily bonded to each other by the vulcanization reaction.

However, the silane coupling agents which are organosilicon compound having an alkoxysilyl group in the molecule has a problem in that an alcohol is formed in the reaction with the inorganic filler such as silica. Foams are formed at the inside of an unvulcanized rubber obtained after extrusion since the formed alcohol is vaporized in the rubber, and dimensional stability and productivity decrease. It is desired that discharge of volatile alcohols is decreased from the standpoint of the health of the producer and the consumer and the consideration on the environment, also.

To overcome the above problem, various coupling agents which are organosilicon compounds suppressing discharge of alcohols have been proposed (Patent References 1 to 3). However, the suppressed discharge of volatile alcohols and the sufficient reactivity with an inorganic filler such as silica are not achieved simultaneously to the desired degree by using the above compounds.

[Patent Reference 1] Japanese Patent Application Laid-Open No. 2002-275311

[Patent Reference 2] Japanese Patent Application Publication (Tokuhyo) No. 2005-500420

[Patent Reference 3] Japanese Patent Application Laid-Open No. 2005-35889

[Patent Reference 4] Japanese Patent Application Laid-Open No. 2000-103794

DISCLOSURE OF THE INVENTION

Problems to be Overcome by the Invention

The present invention has an object of providing an organosilicon compound which simultaneously suppresses discharge of volatile alcohols generated during the reaction with an inorganic filler and exhibits great reactivity with the inorganic filler.

Means for Overcoming the Problems

As the result of intensive studies by the present inventor to achieve the above object, it was found that the above object could be achieved by an organosilicon compound in which the hydrocarbon portion of at least one alkoxyl group had a length within a specific range.

The present invention has been completed based on the knowledge.

The present invention provides an organosilicon compound having a structure represented by following general formula:

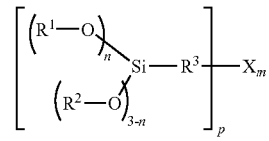

wherein $R^1$ represents methyl group or ethyl group, $R^2$ represents a branched or linear, saturated or unsaturated aliphatic hydrocarbon group having 3 to 8 carbon atoms, n represents a number of 0.5 to 2.5 which shows an average composition, $R^3$ represents a divalent hydrocarbon group selected from —$CH_2$—, —$CH_2CH_2$—, —$CH_2CH_2CH_2$—, —$CH_2CH_2CH_2CH_2$—, —$CH_2CH_2CH_2CH_2CH_2$—, —CH($CH_3$)—, —$CH_2CH(CH_3)$—, —C($CH_3$)$_2$—, —CH($C_2H_5$)—, —$CH_2CH_2CH(CH_3)$— and —$CH_2CH(CH_3)CH_2$—, and X represents an atom or a group selected from S, S(C=O)—$R^4$, SH and $NH_{(3-p)}$, $R^4$ representing a branched or linear, saturated or unsaturated aliphatic hydrocarbon group having 1 to 30 carbon atoms; and p represents 2 and m represents a number of 1 to 10 when X represents S, p represents 1 and m represents 1 when X represents S(C=O)—$R^4$, p represents 1 and m represents 1 when X represents SH, and p represents a number of 1 to 3 and m represents 1 when X represents $NH_{(3-p)}$.

The Effect of the Invention

In accordance with the present invention, an organosilicon compound which simultaneously suppresses discharge of volatile alcohols generated during the reaction with an inorganic filler and exhibits great reactivity with the inorganic filler, a rubber composition comprising the compound and a pneumatic tire prepared by using the rubber composition can be provided.

THE MOST PREFERRED EMBODIMENT TO CARRY OUT THE INVENTION

In the above general formula, as the linear or branched, saturated or unsaturated aliphatic hydrocarbon group having 3 to 8 carbon atoms which is represented by $R^2$, a linear or branched, saturated or unsaturated aliphatic hydrocarbon group having 3 to 7 carbon atoms is preferable, a linear or branched, saturated or unsaturated aliphatic hydrocarbon group having 5 to 7 carbon atoms is more preferable, and a linear or branched, saturated or unsaturated aliphatic hydrocarbon group having 6 or 7 carbon atoms is most preferable. When the number of carbon atom is 1 or 2, the discharge of volatile alcohols is great, and the object of the present invention is not achieved. On the other hand, when the number of carbon atom is 9 or greater, the reactivity with the inorganic filler decreases, and the function as the silane coupling agent cannot be sufficiently exhibited.

The aliphatic hydrocarbon group includes alicyclic hydrocarbon groups. Examples of the group represented by $R^2$ include n-propyl group, isopropyl group, n-butyl group, isobutyl group, sec-butyl group, tert-butyl group, n-pentyl group, isopentyl group, tert-pentyl group, cyclopentyl group, n-hexyl group, isohexyl group, cyclohexyl group, n-heptyl group, isoheptyl group, n-octyl group, 2-ethylhexyl group, isooctyl group, propenyl group, allyl group, various types of butenyl groups, various types of pentenyl groups, cyclopentenyl group, various types of hexenyl groups, cyclohexenyl group, various types of heptenyl groups and various types of octenyl groups. Among these groups, n-hexyl group, isohexyl group, cyclohexyl group, n-heptyl group, isoheptyl group, various types of hexenyl groups, cyclohexenyl groups and various types of heptenyl groups are preferable.

In the above general formula, $-CH_2CH_2CH_2-$, $-CH_2CH_2CH_2CH_2-$ and $-CH_2CH_2CH_2CH_2CH_2-$ are preferable as the divalent hydrocarbon group represented by $R^3$ from the standpoint of the production.

In the organosilicon compound represented by the above general formula, it is preferable that X represents S (sulfur) since the reactivity with the rubber can be suitably controlled by the number represented by m. When X represents S, m represents a number in the range of 1 to 10. The greater the number represented by m, the greater the reactivity with the rubber. When an organosilicon compound represented by the general formula in which m represents 1 is used as the silane coupling agent, it is necessary that the rubber composition comprise a suitable amount of sulfur in combination with the organosilicon compound.

The organosilicon compound of the present invention can be produced in accordance with various conventional processes. For example, in Patent Reference 4, a process in which a high purity sulfur-containing organosilicon compound having a polysulfide structure is obtained in accordance with a simplified process without treatments at a high temperature or under a vacuum, is disclosed. For example, a sulfur-containing organosilicon compound which is an organosilicon compound of the present invention can be obtained by esterification of 3-chloropropyltrichlorosilane with ethanol or a mixture of methanol and an alcohol having a long chain having 3 to 8 carbon atoms, followed by the reaction with an anhydrous alkali sulfide.

The organosilicon compound of the present invention can also be obtained by obtaining a mixture of esters by the reaction of trichlorosilane with ethanol or a mixture of methanol and an alcohol having a long chain having 3 to 8 carbon atoms, followed by hydrosilylation with an allyl halide and then by the reaction with anhydrous alkali sulfide.

As disclosed in Patent Reference 3, the organosilicon compound of the present invention may be produced by transesterification of a silane compound having an alkoxyl group having a short chain (methoxyl group and/or ethoxyl group) with an alcohol having a long chain, followed by continuously removing the formed alcohol having a short chain from the reaction mixture by distillation.

The rubber composition comprising the organosilicon compound of the present invention comprises a rubber component comprising at least one rubber selected from diene-based rubbers, i.e., natural rubber and/or synthetic rubbers. Examples of the synthetic rubbers include isoprene rubber (IR), butadiene rubber (BR), styrene-butadiene copolymer rubber (SBR), ethylene-propylene-diene terpolymer rubber (EPDM), butyl rubber (IIR), halogenated butyl rubber and nitrile rubber (NBR). The above rubber may be used singly or in combination of two or more as described above.

As the inorganic filler used in the rubber composition of the present invention, inorganic fillers containing silicic acid such as silica, aluminosilicates, zeolite, clay and carbon black containing silica fixed on the surface and aluminum hydroxide can be used. Among the above fillers, silica and aluminum hydroxide are preferable. The inorganic fillers described above as the examples may be used singly or in combination of two or more.

The amount of the inorganic filler is preferably 1 to 150 parts by mass, more preferably 3 to 130 parts by mass and most preferably 3 to 90 parts by mass based on 100 parts by mass of the rubber component comprising at least one rubber selected from natural rubber and/or synthetic rubbers and preferably comprising at least one rubber selected from natural rubber and synthetic rubbers as the main component. When the amount of the inorganic filler is within the above range, the effect of the present invention, i.e., the sufficient reinforcing property and workability, can be exhibited. When the amount of the inorganic filler is excessively small, the reinforcing property tends to be poor. When the amount of the reinforcing filler is excessively great, the workability tends to be poor.

As silica used in the rubber composition of the present invention, silica prepared in accordance with the precipitation process is preferable. The BET specific surface area of silica is preferably in the range of 40 to 350 m$^2$/g and more preferably in the range of 70 to 300 m$^2$/g. Examples of silica described above include "NIPSIL AQ" manufactured by NIPPON SILICA KOGYO Co., Ltd., "ULTRASIL VN3" manufactured by DEGUSSA Company, "ZEOSIL 1165 MP", "ZEOSIL 165GR" and "ZEOSIL 175P" manufactured by RHODIA Company, and "HISIL 233", "HISIL 210" and "HISIL 255" manufactured by PPG Company. However, silica is not limited to those described above as the examples.

As aluminum hydroxide used in the rubber composition of the present invention, fine particle products and small particle products of "HIGILITE", a trade name, manufactured by SHOWA DENKO Co., Ltd. are preferable. In the present invention, alumina having aluminum hydroxide on the surface is include in aluminum hydroxide described above.

The amount of the organosilicon compound of the present invention is preferably in the range of 1 to 30% by mass and more preferably in the range of 5 to 20% by mass based on the amount of the inorganic filler described above.

The rubber composition of the present invention may suitably comprise various additives conventionally used in rubber compositions such as vulcanizing agent examples of which include sulfur, vulcanization accelerators, antioxidants, zinc oxide and stearic acid.

EXAMPLES

The present invention will be described more specifically with reference to examples in the following. However, the present invention is not limited to the examples.

The measurement of the porous fraction and the tensile test were conducted in accordance with the following methods.

1. Porous Fraction

A piece of an unvulcanized rubber cut into a size of 5×5×20 mm was heated in an oven at 125° C. for 30 minutes, and the porous fraction was obtained in accordance with the following equation:

porous fraction(%)={(specific gravity before heating/specific gravity after heating)−1}×100

The smaller the obtained value, the better the result of evaluation.

2. Tensile Test

The elongation at break (EB1), the strength at break (TB), the tensile moduli at 50%, 100% and 300% elongations and the toughness (TF) were measured in accordance with the method of Japanese Industrial Standard K6301. The toughness was obtained as the integrated area under the stress-strain curve before the fracture. The above values are shown as indices based on the results in Comparative Example 1 used as the references, which are set at 100.

Preparation Example 1

Synthesis of Organosilicon Compound B
[bis(3-diethoxyhexyloxysilylpropyl)polysulfide]

Into a 200 ml egg-plant-shaped flask, 45 g of bis(3-triethoxysilyl-propyl) polysulfide (in the above general formula, n=3, $R^1$=$R^2$=ethyl group, $R^3$=—$CH_2CH_2CH_2$—, X=S, p=2, and m=2.5; referred to as Organosilicon compound A, hereinafter), 9.3 g of 1-hexyl alcohol and 0.5 g of p-toluenesulfonic acid were placed at the room temperature. The obtained red solution was heated at 100 to 105° C. until no bubbles were formed. Then, 9.3 g of 1-hexyl alcohol was added dropwise from a dropping funnel over 30 minutes. Ethanol was removed using a rotary evaporator at 85° C. under 6,000 Pa, and bis(3-diethoxyhexyloxysilylpropyl)polysulfide (in the above general formula, n=2, $R^1$=ethyl group, $R^2$=$C_6H_{13}$, $R^3$=—$CH_2CH_2CH_2$—, X=S, p=2, and m=2.5) was obtained.

Preparation Example 2

Synthesis of Organosilicon Compound C
[bis(3-diethoxypropyloxysilylpropyl)polysulfide]

Into a 200 ml egg-plant-shaped flask 45 g of Organosilicon compound A, 5.5 g of 1-propyl alcohol and 0.5 g of p-toluenesulfonic acid were placed at the room temperature. The obtained red solution was heated at 100 to 105° C. until no bubbles were formed. Then, 5.5 g of 1-propyl alcohol was added dropwise from a dropping funnel over 30 minutes. Ethanol was removed using a rotary evaporator at 85° C. under 6,000 Pa, and bis(3-diethoxypropyloxysilylpropyl)polysulfide (in the above general formula, n=2, $R^1$=ethyl group, $R^2$=$C_3H_7$, $R^3$=—$CH_2CH_2CH_2$—, X=S, p=2, and m=2.5) was obtained.

Preparation Example 3

Synthesis of Organosilicon Compound D
[bis(3-diethoxydecyloxysilylpropyl)polysulfide]

Into a 200 ml egg-plant-shaped flask 45 g of Organosilicon compound A, 14.5 g of 1-decyl alcohol and 0.5 g of p-toluenesulfonic acid were placed at the room temperature. The obtained red solution was heated at 100 to 105° C. until no bubbles were formed. Then, 14.5 g of 1-decyl alcohol was added dropwise from a dropping funnel over 30 minutes. Ethanol was removed using a rotary evaporator at 85° C. under 6,000 Pa, and bis(3-diethoxyhexyloxysilylpropyl)polysulfide (in the above general formula, n=2, $R^1$=ethyl group, $R^2$=$C_{10}H_{21}$, $R^3$=—$CH_2CH_2CH_2$—, X=S, p=2, and m=2.5) was obtained.

Preparation Example 4

Synthesis of Organosilicon Compound E
[bis(3-trihexyloxysilylpropyl)polysulfide]

Into a 200 ml egg-plant-shaped flask 45 g of Organosilicon compound A, 28.1 g of 1-hexyl alcohol and 0.5 g of p-toluenesulfonic acid were placed at the room temperature. The obtained red solution was heated at 100 to 105° C. until no bubbles were formed. Then, 28.1 g of 1-hexyl alcohol was added dropwise from a dropping funnel over 30 minutes. Ethanol was removed using a rotary evaporator at 85° C. under 6,000 Pa, and bis(3-diethoxyhexyloxysilylpropyl) polysulfide (in the above general formula, n=0, $R^2$=$C_6H_{13}$, $R^3$=—$CH_2CH_2CH_2$—, X=S, p=2, and m=2.5) was obtained.

Examples 1 to 6 and Comparative Examples 1 to 8

Fourteen types of rubber compositions were prepared in accordance with the formulations shown in Table 1 under a conventional condition of mixing. The porous fraction was measured using unvulcanized rubber compositions, and the tensile test was conducted using vulcanized rubber compositions. The results are shown in Table 1.

TABLE 1

| Example | | | 1 | 2 | | 3 | | 4 |
|---|---|---|---|---|---|---|---|---|
| Comparative Example | 1 | 2 | | | 3 | | 4 | |

| | | | [Formulation] | | | | | |
|---|---|---|---|---|---|---|---|---|
| Emulsion polymerized SBR *[1] | 100 | 100 | 100 | 100 | 100 | 100 | 100 | 100 |
| Carbon black N220 *[2] | 10 | 10 | 10 | 10 | 10 | 10 | 50 | 50 |
| Silica *[3] | 50 | 50 | 50 | 50 | 50 | 50 | — | — |
| Aluminum hydroxide *[4] | — | — | — | — | 10 | 10 | 10 | 10 |
| Organosilicon compound A | 3 | 4.5 | — | — | 4.5 | — | 1.0 | — |
| Organosilicon compound B [note] | — | — | 3.7 | 5.5 | — | 5.5 | — | 1.0 |
| Organosilicon compound C [note] | — | — | — | — | — | — | — | — |
| Organosilicon compound D [note] | — | — | — | — | — | — | — | — |
| Organosilicon compound E [note] | — | — | — | — | — | — | — | — |

TABLE 1-continued

| | | | | | | | | |
|---|---|---|---|---|---|---|---|---|
| Aromatic oil | 30 | 30 | 30 | 30 | 30 | 30 | 30 | 30 |
| Stearic acid | 2.0 | 2.0 | 2.0 | 2.0 | 2.0 | 2.0 | 2.0 | 2.0 |
| Antioxidant 6PPD *5 | 1.0 | 1.0 | 1.0 | 1.0 | 1.0 | 1.0 | 1.0 | 1.0 |
| Antioxidant TMDQ *6 | 1.0 | 1.0 | 1.0 | 1.0 | 1.0 | 1.0 | 1.0 | 1.0 |
| Zinc oxide | 2.5 | 2.5 | 2.5 | 2.5 | 2.5 | 2.5 | 2.5 | 2.5 |
| Vulcanization accelerator DPG *7 | 0.6 | 0.6 | 0.6 | 0.6 | 0.6 | 0.6 | 0.6 | 0.6 |
| Vulcanization accelerator MBTS *8 | 1.0 | 1.0 | 1.0 | 1.0 | 1.0 | 1.0 | 1.0 | 1.0 |
| Vulcanization accelerator TBBS *9 | 0.6 | 0.6 | 0.6 | 0.6 | 0.6 | 0.6 | 0.6 | 0.6 |
| Sulfur | 2.0 | 2.0 | 2.0 | 2.0 | 2.0 | 2.0 | 2.0 | 2.0 |
| Porous fraction (%) | 7 | 8 | 0 | 0 | 9 | 0 | 2 | 0 |
| Tensile test | | | | | | | | |
| elongation at break (EB1) | 100 | 97 | 103 | 95 | 98 | 98 | 110 | 111 |
| strength at break (TB) | 100 | 100 | 105 | 100 | 99 | 99 | 112 | 112 |
| tensile modulus at 50% | 100 | 105 | 100 | 104 | 102 | 102 | 104 | 103 |
| tensile modulus at 100% | 100 | 108 | 101 | 108 | 105 | 104 | 109 | 110 |
| tensile modulus at 300% | 100 | 107 | 103 | 112 | 107 | 106 | 109 | 107 |
| toughness (TF) | 100 | 97 | 110 | 98 | 98 | 98 | 115 | 116 |

| | Example | | Comparative Example | | | |
|---|---|---|---|---|---|---|
| | 5 | 6 | 5 | 6 | 7 | 8 |
| [Formulation] | | | | | | |
| Emulsion polymerized SBR *1 | 100 | 100 | 100 | 100 | 100 | 100 |
| Carbon black N220 *2 | 10 | 10 | 10 | 10 | 10 | 10 |
| Silica *3 | 50 | 50 | 50 | 50 | 50 | 50 |
| Aluminum hydroxide *4 | — | — | — | — | — | — |
| Organosilicon compound A note) | — | — | — | — | — | — |
| Organosilicon compound B note) | — | — | — | — | — | — |
| Organosilicon compound C note) | 3.1 | 4.7 | — | — | — | — |
| Organosilicon compound D note) | — | — | 4.2 | 6.3 | — | — |
| Organosilicon compound E note) | — | — | — | — | 4.8 | 7.1 |
| Aromatic oil | 30 | 30 | 30 | 30 | 30 | 30 |
| Stearic acid | 2.0 | 2.0 | 2.0 | 2.0 | 2.0 | 2.0 |
| Antioxidant 6PPD *5 | 1.0 | 1.0 | 1.0 | 1.0 | 1.0 | 1.0 |
| Antioxidant TMDQ *6 | 1.0 | 1.0 | 1.0 | 1.0 | 1.0 | 1.0 |
| Zinc oxide | 2.5 | 2.5 | 2.5 | 2.5 | 2.5 | 2.5 |
| Vulcanization accelerator DPG *7 | 0.6 | 0.6 | 0.6 | 0.6 | 0.6 | 0.6 |
| Vulcanization accelerator MBTS *8 | 1.0 | 1.0 | 1.0 | 1.0 | 1.0 | 1.0 |
| Vulcanization accelerator TBBS *9 | 0.6 | 0.6 | 0.6 | 0.6 | 0.6 | 0.6 |
| Sulfur | 2.0 | 2.0 | 2.0 | 2.0 | 2.0 | 2.0 |
| Porous fraction (%) | 0 | 0 | 0 | 0 | 0 | 0 |
| Tensile test | | | | | | |
| elongation at break (EB1) | 103 | 102 | 90 | 89 | 92 | 93 |
| strength at break (TB) | 101 | 102 | 81 | 82 | 78 | 79 |
| tensile modulus at 50% | 100 | 105 | 89 | 92 | 88 | 90 |
| tensile modulus at 100% | 101 | 108 | 88 | 91 | 87 | 89 |
| tensile modulus at 300% | 103 | 105 | 89 | 93 | 86 | 85 |
| toughness (TF) | 103 | 100 | 80 | 86 | 82 | 83 |

Note) In place of Organosilicon compound A, Organosilicon compounds B, C, D and E were used each in the same amount by mole.
*1 Manufactured by JSR Co., Ltd., emulsion polymerized SBR, #1500
*2 Manufactured by ASAHI CARBON Co., Ltd., #80
*3 Manufactured by NIPPON SILICA KOGYO Co., Ltd., NIPSIL AQ
*4 Manufactured by SHOWA DENKO Co., Ltd., a fine particle product of HIGILITE
*5 N-(1,3-Dimethylbutyl)-N'-phenyl-p-phenylenediamine, manufactured by OUCHI SHINKO KAGAKU KOGYO Co., Ltd., NOCRAC 6C
*6 A polymerized product of 2,2,4-trimethyl-1,2-dihydroquinoline, manufactured by OUCHI SHINKO KAGAKU KOGYO Co., Ltd., NOCRAC 224
*7 Diphenylguanidine, manufactured by SANSHIN KAGAKU KOGYO Co., Ltd., SANCELOR D
*8 Dibenzothiazyl disulfide, manufactured by SANSHIN KAGAKU KOGYO Co., Ltd., SANCELOR DM
*9 N-tert-Butyl-2-benzothiazolylsulfenamide, manufactured by SANSHIN KAGAKU KOGYO Co., Ltd., SANCELOR NS As clearly shown by comparing the rubber compositions in Examples 1 and 5 with the rubber composition in Comparative Example 1, the rubber compositions in Examples 2 and 6 with the rubber composition in Comparative Example 2, the rubber composition in Example 3 with the rubber composition in Comparative Example 3, and the rubber composition in Example 4 with the rubber composition in Comparative Example 4, by using the organosilicon compounds of the present invention in Examples 1 to 6, the properties of the vulcanized products were maintained at the same level as those obtained by using the organosilicon compounds of Comparative Examples 1 to 4 and porous fractions were greatly decreased from those obtained by using the organosilicon compounds of Comparative Example 1 to 4.

As shown by the results in Comparative Examples 5 and 6, when the carbon chain in the group represented by $R^2$ was longer than the specified range, the reaction between the silane and silica was adversely affected due to the increase in the steric hindrance, and the tensile modulus and the strength at break decreased. As shown in Comparative Examples 7 and 8, when n=0, the reaction between the silane and silica was adversely affected due to the increase in the steric hindrance, and the tensile modulus and the strength at break decreased.

INDUSTRIAL APPLICABILITY

The organosilicon compound of the present invention is advantageously used as the silane coupling agent for rubber compositions comprising an inorganic filler which are used for treads of various pneumatic tires and, in particular, for pneumatic radial tires, for passenger cars, small trucks, light passenger cars, light trucks and large vehicles.

The invention claimed is:

1. An organosilicon compound having a structure represented by following general formula:

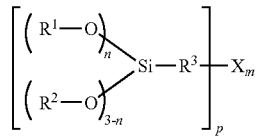

wherein $R^1$ represents methyl or ethyl group, $R^2$ represents a branched or linear, saturated or unsaturated aliphatic hydrocarbon group having 5 to 7 carbon atoms, n represents a number of 0.5 to 2.5 which shows an average composition, $R^3$ represents a divalent hydrocarbon group selected from —$CH_2$—, —$CH_2CH_2$—, —$CH_2CH_2CH_2$—, —$CH_2CH_2CH_2CH_2$—, —$CH_2CH_2CH_2CH_2CH_2$—, —CH($CH_3$)—, —$CH_2$CH($CH_3$)—, —C($CH_3$)$_2$—, —CH($C_2H_5$)—, —$CH_2CH_2$CH($CH_3$)— and —$CH_2$CH($CH_3$)$CH_2$—, X represents S, p represents 2 and m represents a number of 1 to 10.

2. A rubber composition which comprises a rubber component comprising at least one rubber selected from natural rubber and synthetic rubbers, an inorganic filler in an amount of 1 to 150 parts by mass based on 100 parts by mass of the rubber component and the organosilicon compound described in claim 1 in an amount of 1 to 30% by mass based on the amount of the inorganic filler.

3. A rubber composition according to claim 2, wherein the inorganic filler is silica and/or aluminum hydroxide.

4. A pneumatic tire prepared by using the rubber composition described in claim 2.

5. A pneumatic tire prepared by using the rubber composition described in claim 3.

* * * * *